(12) United States Patent
Miesel

(10) Patent No.: US 6,221,024 B1
(45) Date of Patent: Apr. 24, 2001

(54) IMPLANTABLE PRESSURE SENSOR AND METHOD OF FABRICATION

(75) Inventor: Keith A. Miesel, St. Paul, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/119,095

(22) Filed: Jul. 20, 1998

(51) Int. Cl.⁷ .................................................. A61B 5/00

(52) U.S. Cl. ......................................... 600/486; 600/488

(58) Field of Search ................................ 600/486, 488; 607/23

(56) References Cited

U.S. PATENT DOCUMENTS

| | | | |
|---|---|---|---|
| 3,939,823 | 2/1976 | Kaye et al. | 128/2 S |
| 4,023,562 | 5/1977 | Hynecek | 128/2.05 E |
| 4,407,296 | 10/1983 | Anderson | 128/675 |
| 4,432,372 | 2/1984 | Monroe | 128/675 |
| 4,485,813 | 12/1984 | Anderson et al. | 128/675 |
| 4,610,256 * | 9/1986 | Wallace | 600/488 |
| 4,858,615 | 8/1989 | Menema | 128/668 |
| 4,967,755 | 11/1990 | Pohndorf | 128/675 |
| 5,040,544 | 8/1991 | Lessar | 128/784 |
| 5,324,326 | 6/1994 | Lubin | 607/122 |
| 5,461,922 * | 10/1995 | Koen | 600/488 |
| 5,807,265 * | 9/1998 | Itoigawa et al. | 600/486 |

FOREIGN PATENT DOCUMENTS

| | | | |
|---|---|---|---|
| WO 94/13200 | 6/1994 | (WO) | A61B/5/03 |

OTHER PUBLICATIONS

Ko et al., "A Design of Capacitive Presure Transducer", IEEE Proc. Symp. Biosensors 1984 p. 32.
Graeger et al., "A Ceramic Differential–Pressure Transducer", Philips Tech. Rev., 43:4:86–93 Feb. 1987.

* cited by examiner

Primary Examiner—Robert L. Nasser
(74) Attorney, Agent, or Firm—Michael B. Atlass; Harold R. Patton (57) ABSTRACT

A body implantable pressure sensor attached to an endocardial lead for implantation in a heart chamber or cardiac blood vessel for sensing blood pressure and providing blood pressure signals to an implanted or external hemodynamic monitor and/or therapy delivery device and method of fabrication thereof. A pressure sensor module is formed of an elongated receptacle having an elongated receptacle cavity for receiving a calibrated, micro-machined pressure transducer having a pressure responsive element. The receptacle cavity is covered by a diaphragm disposed alongside the lead body and in parallel with the lead axis. The receptacle cavity is filled with a incompressible oil for transferring pressure forces that are applied to the diaphragm to the pressure transducer. The oil is introduced through a fill port, and the fill port is sealed after the oil is introduced to prevent leakage of the oil from the receptacle cavity and to complete the hermetic sealing of the receptacle cavity. The fill port further comprises a fill tube having a fill tube lumen extending outward of an end wall of the receptacle cavity to a fill tube end, and said sealing step further comprises the steps of crimping or otherwise obstructing the fill tube end to close the fill tube lumen, fitting a fill port cover having an abutting edge over the crimped fill tube end and against the end wall of the receptacle to enclose the sealed fill tube end within a fill port cover cavity, and sealing the abutting edge against the receptacle end wall to hermetically enclose the sealed fill tube end within the fill port cover cavity.

4 Claims, 6 Drawing Sheets

IMPLANTABLE PRESSURE SENSOR AND METHOD OF FABRICATION

FIELD OF THE INVENTION

The present invention relates to a body implantable pressure sensor attached to an endocardial lead for implantation in a heart chamber or cardiac blood vessel for sensing blood pressure and providing blood pressure signals to an implanted or external hemodynamic monitor and/or therapy delivery device and method of fabrication thereof.

DESCRIPTION OF THE BACKGROUND ART

Efforts have been underway for many years to develop implantable pressure transducers and sensors for temporary or chronic use in a body organ or vessel and systems for recording absolute pressure. Many different designs and operating systems have been proposed and placed into temporary or chronic use with patients. Indwelling pressure sensors for temporary use of a few days or weeks are available, and many designs of chronically or permanently implantable pressure sensors have been placed in clinical use.

U.S. Pat. No. 4,023,562 describes a pressure transducer comprising a piezoresistive bridge of four, orthogonally disposed, semiconductor strain gauges formed interiorly on a single crystal silicon diaphragm area of a silicon base. A protective silicon cover is bonded to the base around the periphery of the diaphragm area to form a sealed, evacuated chamber. Deflection of the diaphragm due to ambient pressure changes is detected by the changes in resistance of the strain gauges. Because the change in resistance is so small, a high current is required to detect the voltage change due to the resistance change. The high current requirements render the piezoresistive bridge unsuitable for long term use with an implanted power source. High gain amplifiers that are subject to drift over time are also required to amplify the resistance-related voltage change.

Other semiconductor pressure transducers employ CMOS IC technology in the fabrication of pressure responsive silicon diaphragm bearing capacitive plates that are spaced from stationary plates. The change in capacitance due to pressure waves acting on the diaphragm is measured, typically through a bridge circuit, as disclosed, for example, in the article "A Design of Capacitive Pressure Transducer" by Ko et al., in *IEEE Proc. Symp. Biosensors*, 1984, p. 32. Again, fabrication for long term implantation and stability is complicated. In addition, differential capacitive plate, fluid filled pressure transducers employing thin metal or ceramic diaphragms have also been proposed for large scale industrial process control applications as disclosed, for example, in the article, "A ceramic differential-pressure transducer" by Graeger et al., *Philips Tech. Rev.*, 43:4:86–93, February 1987. The large scale of such pressure transducers does not lend itself to miniaturization for chronic implantation.

Piezoelectric crystal or piezoresistive pressure transducers mounted at or near the distal tips of pacing leads, for pacing applications, or catheters for monitoring applications, are described in U.S. Pat. Nos. 4,407,296, 4,432,372, 4,485,813, 4,858,615, 4,967,755, and 5,324,326, and PCT Publication No. WO 94/13200, for example. The desirable characteristics and applications for patient use of such lead or catheter bearing, indwelling pressure sensors are described in these and other patents and the literature in the field. Generally, the piezoelectric or piezoresistive transducers have to be sealed hermetically from blood.

The '296 patent discloses sealing the piezoresistive bridge elements within an oil filled chamber having a deflectable diaphragm so that blood pressure fluctuations can deflect the diaphragm and be transmitted by the oil to the pressure transducer. In one embodiment disclosed therein, a sealed inner chamber at a calibrated pressure is provided on one side of the piezoresistive bridge transducer, and the oil bears against the other side of the transducer. The incompressible oil is admitted into the chamber through a fill tube in a vacuum filling process to fill the chamber between the transducer and the diaphragm. The fill tube is then crimped.

The crimping of the end of the fill tube is not necessarily sufficient to prevent leakage of the oil from the chamber. Such pressure sensor leads are intended to be chronically implanted in patients for years or decades. The function of the pressure transducer will be impaired if the oil leaks from the chamber and is displaced by air or body fluids over such a period of time.

Moreover, the configuration of the pressure transducer housing employed in the '296 patent locates the diaphragm perpendicular to the lead body axis and facing distally. This constitutes a bulky transducer module and prevents its use at a location more proximal to the distal end of the lead body.

Despite the considerable effort that has been expended in designing such pressure sensors, a need exists for a body implantable, durable, long-lived and low power consuming pressure sensor for accurately sensing absolute pressure waves in the body over many years and for deriving body temperature signals in a system for demodulating and storing the signals.

SUMMARY OF THE INVENTION

It is therefore an object of the present invention to provide an improved method for sealing oil filled pressure transducer modules for a chronically implantable pressure sensor lead.

The present invention involves a body implantable pressure sensor attached to an endocardial lead for implantation in a heart chamber or cardiac blood vessel for sensing blood pressure and providing blood pressure signals to an implanted or external hemodynamic monitor and/or therapy delivery device and method of fabrication thereof. A pressure sensor module is formed of an elongated receptacle having an elongated receptacle cavity for receiving a calibrated, micro-machined pressure transducer having a pressure responsive element. The receptacle cavity is covered by a diaphragm disposed alongside the lead body and in parallel with the lead axis. The receptacle cavity is filled with a incompressible oil for transferring pressure forces that are applied to the diaphragm to the pressure transducer. The oil is introduced through a fill port, and the fill port is sealed after the oil is introduced to prevent leakage of the oil from the receptacle cavity and to complete the hermetic sealing of the receptacle cavity. In one embodiment, the fill port comprises a fill tube having a fill tube lumen extending outward of an end wall of the receptacle cavity to a fill tube end, and said sealing step further comprises the steps of crimping the fill tube end to close the fill tube lumen, fitting a fill port cover having an abutting edge over the crimped fill tube end and against the end wall of the receptacle to enclose the crimped fill tube end within a fill port cover cavity, and sealing the abutting edge against the receptacle end wall to hermetically enclose the sealed fill tube end within the fill port cover cavity.

In another embodiment, the fill port is formed with a tapered fill port lumen and is closed by a stopper pressed into it to close or block the fill port lumen and inhibit leakage of oil therethrough. The closed fill port is then enclosed within the fill port cover in the same manner.

Moreover, the fill tube lumen can be tapered and receive a stopper and these closure techniques can be combined.

The crimping or blocking of the fill tube does not overpressurize the oil within the receptacle cavity. In addition, the sealing of the abutting edge against the receptacle obviates the need for welding of the crimped or blocked fill tube end. The welding energy applied to the fill tube end can overheat the oil within the receptacle cavity that can result in expansion of the oil and damage to the pressure transducer and/or to the receptacle and diaphragm or explosion of the oil from the receptacle cavity in extreme cases.

BRIEF DESCRIPTION OF THE DRAWINGS

These and other objects, advantages and features of the present invention will be appreciated as the same becomes better understood by reference to the following detailed description of the preferred embodiment of the invention when considered in connection with the accompanying drawings, in which like numbered reference numbers designate like parts throughout the figures thereof, and wherein.

DETAILED DESCRIPTION OF THE PREFERRED EMBODIMENTS OF THE INVENTION

A preferred embodiment of the present invention is described herein that includes a pressure sensor module that is integrally formed into a pressure sensing lead adapted to be used for sensing blood pressure in a heart chamber and also preferably includes a pace/sense electrode and electrical lead connections of a pacing lead. However, it will be understood that the pressure sensing lead may be constructed as described herein without the pace/sense electrode or that it can be constructed with a cardioversion/defibrillation electrode. In addition, it may be included in a lead bearing another physiological sensor.

Figure 1:
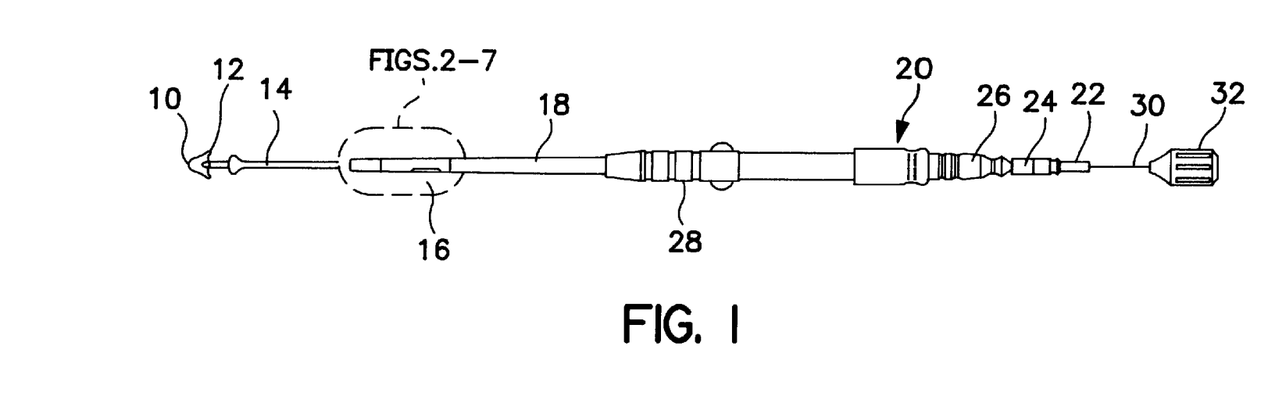
FIG. 1 shows a plan view of a pressure sensing lead according to the present invention.

FIG. 1 illustrates an exemplary pressure sensing lead in accordance with the present invention. The pressure sensing lead is formed of a proximal connector assembly 20 extending between an elongated proximal lead body section 18 to a pressure sensor module 16 and a distal lead body section 14 extending between the pressure sensor module 16 and the distal end of the lead. The lead has a lead body axis, and a distal location for attachment with a pressure sensor module 16 is defined. A pace/sense electrode 10 is located at the distal end of the pressure sensing lead and is coupled by one lead conductor extending the full length of the proximal and distal lead body sections 18 and 14, respectively to a connector pin element 22. Distal electrode 10 is used in conjunction with a further indifferent electrode to apply pacing pulses to the heart tissue or to sense cardiac electrical activity. Electrode 10 is held in engagement with heart tissue by means of passive fixation, flexible tines 12, which engage with the trabeculae in the apex of the ventricle of the heart or in the atrial appendage. A flexible insulating sheath 14 extends from electrode 10 to the distal location where pressure sensor module 16 is located. In a bipolar pace/sense lead configuration, the exterior surface of pressure sensor module 16 can be coupled with an indifferent, ring shaped, pace/sense electrode.

The proximal lead body section 18 that extends proximally from pressure sensor module 16 to the connector assembly 20 located at the proximal end of the lead surrounds three conductors and a stylet lumen. The three conductors are preferably each separately insulated and are wound in a common diameter coil and in an interleaved manner as shown in commonly assigned U.S. Pat. Nos. 5,007,435 and 5,040,544, both incorporated by reference. The three conductors surround a stylet lumen which extends from a lumen of the connector pin element 22 through the proximal lead body section 18, alongside the pressure sensor module 16, and through the distal lead body section 14 to the lead distal end. A stylet 30 having a proximal end knob 32 is shown inserted into the stylet lumen and extending through the length of the lead body to stiffen the lead body and aid in introduction of the distal tip electrode 10 to a site in a heart chamber in a manner well known in the art.

Figure 2:
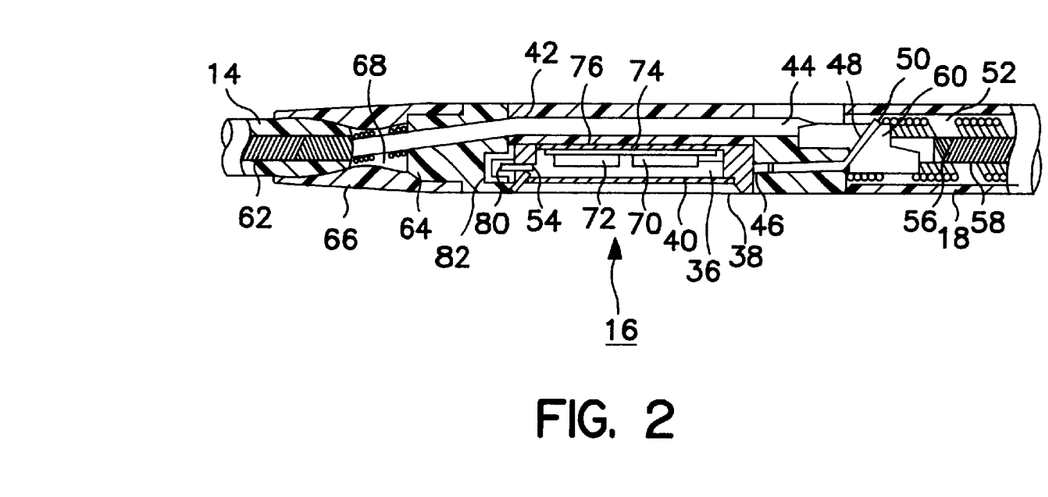
FIG. 2 is a side, cross-section view of the pressure sensor module and electrical connections therewith of FIG. 1.
Figure 3:
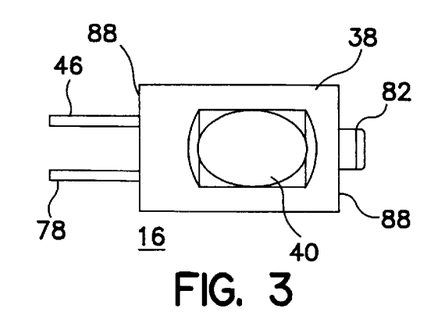
FIG. 3 is a top view of a completed pressure sensor module employed in the pressure sensing lead of FIG. 1.
Figure 4:
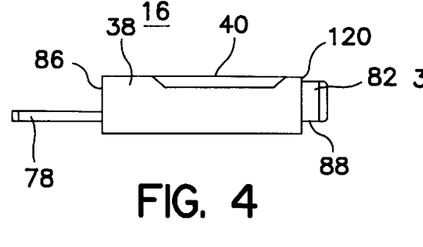
FIG. 4 is a side view of a completed pressure sensor module employed in the pressure sensing lead of FIG. 1.
Figure 5:
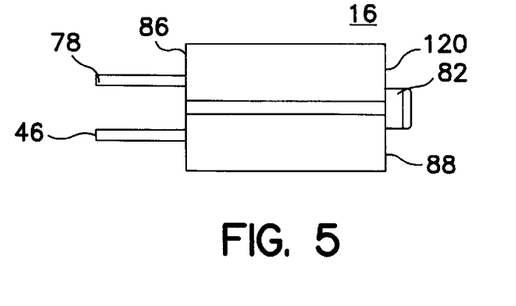
FIG. 5 is a bottom view of a completed pressure sensor module employed in the pressure sensing lead of FIG. 1.
Figure 6:
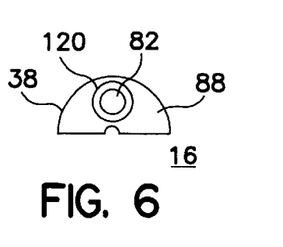
FIGS. 6 and 7 are end views of a completed pressure sensor module employed in the pressure sensing lead of FIG. 1.
Figure 7:
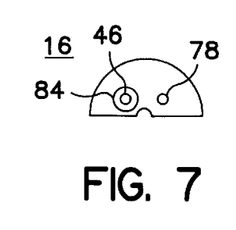

The construction of the proximal lead body section 18 is depicted in FIG. 2. The three conductors are depicted as an outer, multi-polar wire coil 52 and an inner, single pole coiled wire conductor 56 that surrounds the stylet lumen. The outer, multi-polar wire coil 52 is separated from the inner, single pole wire coil 56 by an insulating sheath 58. An outer insulating sheath surrounds the outer, multi-polar wire coil 52. The outer, multi-polar wire coil 52 comprises a pair of coiled wire conductors 48 and 50 that are separately insulated and wound in an interleaved manner.

Connector assembly 20, described in more detail in the above-incorporated '435 patent, is formed with the connector pin element 22 and with two connector ring elements 24 and 26. Connector ring elements 26 and 24 are coupled with coiled wire conductors that extend through the proximal lead body section to and are electrically connected with the pressure sensor transducer IC within pressure sensor module 16. An anchoring sleeve 28 that is used to secure the lead at its point of venous insertion site surrounds the proximal lead body section 18.

The pressure sensor module 16 includes a pressure transducer and electronic IC located within an oil filled receptacle cavity of a receptacle that is covered by a diaphragm as described below. The pressure sensor module can be used for various applications including simply recording and monitoring pressure data wherever it is located, or for sensing blood pressure within the heart in particular. Such measurements can be used to modulate the pacing rate of a cardiac pacemaker, for example as described in the above-incorporated 813 patent. An electrical current would be applied to connector ring elements 24 and 26 during operation of the pressure transducer located within pressure sensor module 16. The capacitance sensed by the pressure transducer will vary depending upon the ambient pressure impinging upon a diaphragm of the pressure sensor module 16. The variance in capacitance can be used by the monitor or pulse generator attached to these connector ring elements to determine blood pressure within the heart chamber at the time of sensor activation.

Figure 8:
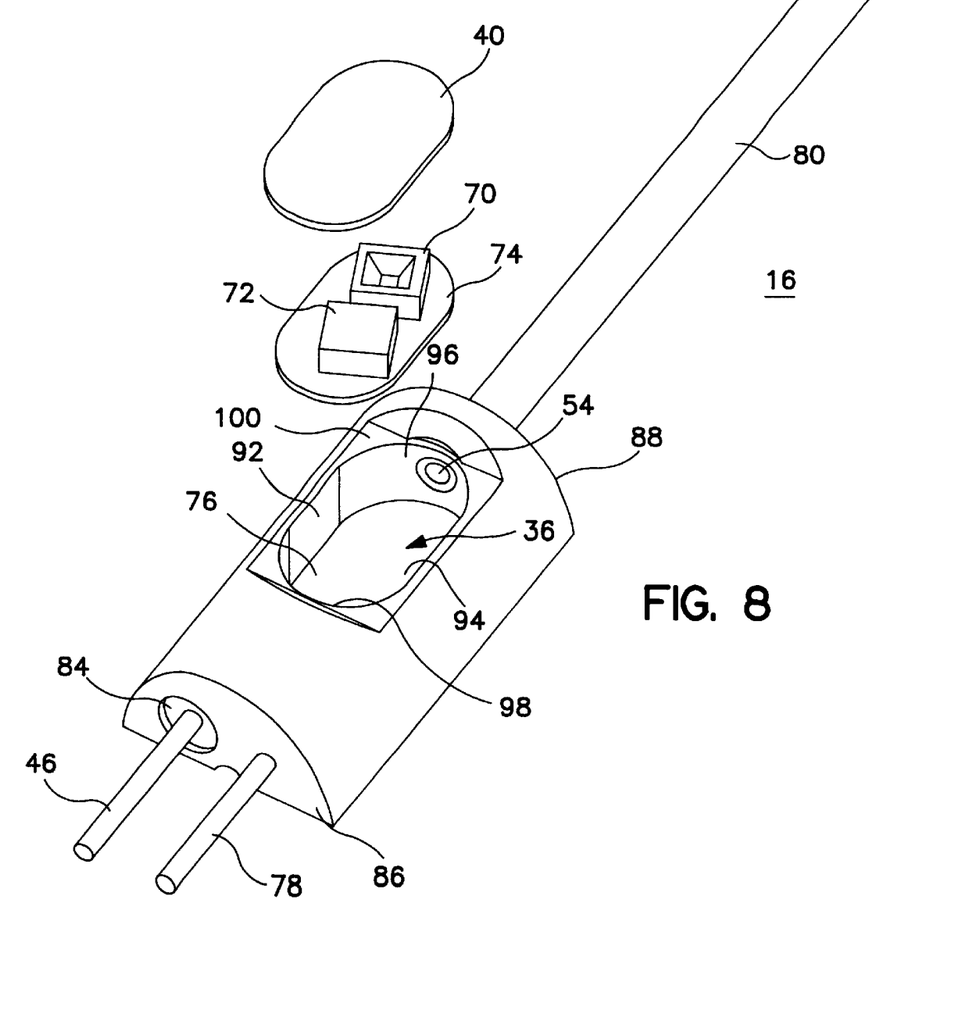
FIG. 8 is an exploded perspective view of the steps of locating the pressure transducer and associated circuit in the receptacle cavity of a receptacle and the attachment of a cover and diaphragm to the frame surrounding the opening into the receptacle cavity.

The mechanical interrelation of components of the pressure sensor module 16 at the distal location of the lead body intermediate the proximal and distal lead body sections 18 and 14 following completion of the assembly of the pressure sensing lead of FIG. 1 is shown in FIG. 2. The completed pressure sensor module 16 is shown in FIGS. 3–7 and in the exploded view of FIG. 8. In these figures, a receptacle 38, which generally takes the form of one-half of a cylinder with a semicircular cross-section, is machined from a section of titanium rod or a similar bio-compatible metal into a half section as best seen in FIGS. 3–8. An elongated receptacle cavity 36 is machined into the curved exterior surface for receiving a calibrated, micro-machined pressure sensor transducer 70 and sensor electronic IC 72 as best seen in FIGS. 2 and 8. A diaphragm 40 operates as a cover over the opening into the receptacle cavity 36 when welded against a frame surrounding the opening into the receptacle cavity 36.

The receptacle 38 occupies about one-half section of the circular cross-section of the lead as shown in FIGS. 1 and 2, and the remaining half section is filled with an insulating material 42 surrounding a tubular stylet guide 44 as shown in FIG. 2. A ring electrode (not shown) can be fitted around the two half sections and electrically attached to the receptacle 38. An opening can be provided in the ring electrode that is aligned with the diaphragm 40 to allow blood to contact it.

A calibrated, micro-machined pressure sensor transducer 70 and sensor electronic IC 72 are mounted on a substrate 74 and are electrically connected together as a sub-assembly that is mounted to a flat base 76 of the receptacle cavity 36 as shown in FIGS. 2 and 8. Two electrical connections extend from the sensor electronic IC 72 to the lead conductors 48 and 50 of multi-polar coiled wire 52 as shown in FIG. 2 through pins 46 and 78 (obscured in FIG. 2). One electrical connection is made to feedthrough pin 46 that extends through a glass or sapphire feedthrough ferrule 84 in a proximal end wall 86 of the receptacle 38 and the other electrical connection is made to the receptacle 38. The proximal end of the feedthrough pin 46 is welded to the distal end of coiled wire conductor 48. The distal end of the other coiled wire conductor 50 is welded to a pin 78 extending from proximally from the proximal end wall 86 of the receptacle 38.

As shown in FIG. 2, the proximal end of stylet tube 44 is fitted within the lumen and coupled to the distal end of multi-filar coiled wire conductor 56. The distal ends of the coiled wire conductors 48 and 50 of the multi-polar coil 52, the multi-filar coil wire conductor 56 and the insulating sheath 58 and the proximal end of the stylet tube 44 are retained in their respective positions relative to one another by means of a plastic spacer 60. The area between the proximal end wall of receptacle 38 and spacer 60, including these electrical connections is backfilled with medical adhesive to further stabilize the structure.

The distal end of stylet tube 44 is fitted into the lumen of and electrically coupled to the proximal end of a second multi-filar coil 62 which extends distally from stylet tube 44 to the distal end of the lead, where it is coupled to tip electrode 10 (FIG. 1). A second plastic spacer 64, in conjunction with a tapered insulating sheath segment 66, maintains the orientation of stylet tube 44 and second multi-filar coil 62. The second plastic spacer 64 includes a space for the cover 82 to fit into. This area and the area 68 surrounding the distal end of stylet tube 44 may be advantageously backfilled with adhesive, if desired, to further stabilize the assembly. The end to end attachment of the stylet tube 44 with the distal and proximal ends of the first and second multi-filar coils 56 and 62 allows insertion of the stylet 30 through the aligned lumens and to the distal tip of the lead.

The receptacle cavity 36 is filled with an incompressible fluid, e.g., a non-conductive oil, for transmitting pressure applied outside the receptacle 38 and against the diaphragm 40 to the pressure responsive element of the pressure transducer 70. The fluid is introduced through a fill port 54 in the distal end wall of the receptacle 38. The fill port includes a distally extending tube 80 enclosed within a cover 82 which is attached to the distal side wall of the receptacle. The cover 82 seals the fill port 54 after introduction of the incompressible fluid into the receptacle cavity 36 to prevent leakage of the fluid from the receptacle cavity 36 and to complete the hermetic sealing of said receptacle cavity 36.

The receptacle 38, the diaphragm 40, the cover 82 and any attached ring electrode are all preferably made of conductive, bio-compatible metals such as titanium, stainless steel, MP35N alloy, or platinum. The resilient plastic member 36, and the illustrated sheathes are preferably fabricated of a bio-compatible plastic such as silicone rubber or polyurethane. Plastic spacers 60 and 64 are preferably fabricated of relatively rigid, preferably bio-compatible plastics such as epoxy or Delrin® (an acetyl co-polymer plastic from Du Pont).

The completed pressure sensor module 16 is illustrated in FIGS. 3–7, and FIG. 8 illustrates the components of the pressure sensor module 16 and how they are fitted together in an initial manufacturing process. As shown in FIG. 8, the receptacle cavity 38 is formed of a relatively flat base 76, oppositely disposed side walls 92 and 94 and oppositely disposed, curved end walls 96 and 98 extending away from the base 74 to the flat oval frame 100 surrounding the opening to the receptacle cavity 36 adapted to be covered by the diaphragm 40. The frame 100 and the diaphragm 40 are parallel with the base 76 and with the lead body axis when the assembly is completed as shown in FIGS. 1 and 2.

The fill port 54 extends through the distal end wall 88 of the receptacle 38 and through the end wall 96 and into the receptacle cavity 36 as illustrated in FIG. 8. The fill port 54 further comprises a fill tube 80 having a fill tube lumen extending the fill port 54 distally from the receptacle distal end wall 88.

To recapitulate with respect to FIG. 8, the sub-assembly of the pressure sensor transducer 70, the electronic IC 72 and the substrate 74 is first assembled and then fitted into the receptacle cavity 36 and adhered to the base 76. The electrical connections with the pins 46 and 78 are completed as described above. The diaphragm 40 is then fitted against and welded to the frame 100, resulting in the pressure sensor module illustrated in FIGS. 3–7. At this stage in the manufacturing process, the remaining space in the receptacle cavity 36 is filled with air.

Figure 9:
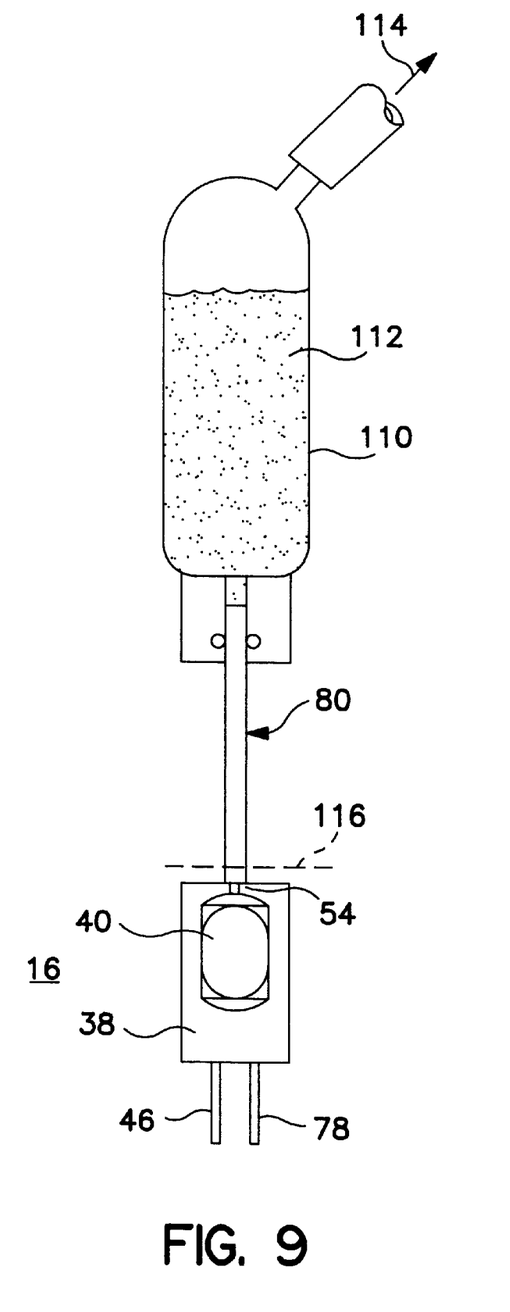
FIG. 9 is a schematic illustration of the filling of the receptacle cavity with incompressible oil.

Then, in accordance with the invention, the air is displaced as the receptacle cavity 36 is filled with the non-compressible fluid 112 through the fill port 54 extending from receptacle cavity 36 through the distal end wall 88 and the lumen of fill tube 80. The fluid 112 is applied through a gravity feed from the fluid container 110, and the flow is effected by drawing a vacuum in the fluid container. Air is drawn upward through the fill tube lumen and fill port 54 as fluid 112 flows downward through the fill tube lumen and fill port 54. All air bubbles are thereby displaced from the fill port 54 and the receptacle cavity 36.

When filling is completed, the fill port 54 is sealed in one of two illustrated ways resulting in a shortening of the fill tube 80 and closure of its lumen. Then, the cover 82 is applied over it and against the distal end wall 88 and sealed thereto. The cover 82 has a cover cavity just large enough to receive the shortened and sealed fill tube end in it and an abutting circular edge 83 that is adapted to be received into a circular recess 89 and fitted against the distal end wall 88. A seal 120 is effected around the area of contact of the abutting circular edge 83 with the circular recess 89 by welding or other sealing methods to hermetically enclose the fill tube end within the fill port cover cavity.

Figure 10:
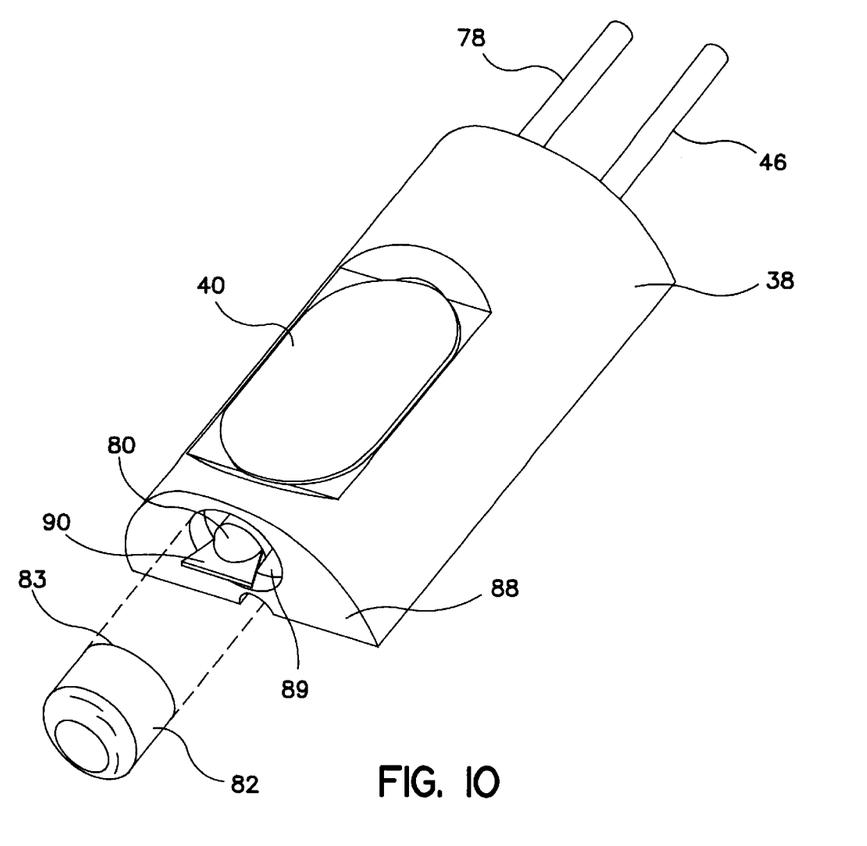
FIG. 10 is an exploded perspective view of the crimped end of the filler tube and a cover that is fitted over it and sealed to the end wall of the receptacle as shown in FIGS. 3–6.

In one embodiment illustrated in FIG. 10, the fill tube 80 is cut and crimped to form a crimped distal end 90 to close the fill tube lumen and seal the fill tube to prevent leakage of fluid from the receptacle cavity 36 to the extent possible. In a further embodiment illustrated in FIG. 11, the fill tube 80 is not used, but the fill port 54 has a fill port lumen 104 that is elongated and tapered inward so that its diameter decreases toward the receptacle cavity. A plug or stopper 102, that is preferably spherical and has a diameter that allows it to be received into the open end of the fill port lumen 104, is inserted into the tapered fill port lumen open end and forced toward the receptacle cavity 36 to make an interference fit with the fill port lumen 104 to seal the fill port 54. Then, the cover 82 is attached and sealed as described above to contain any leakage of oil.

In both cases, redundant sealing of the fill tube 80 or fill port 54 provides added assurance that the fluid will not leak from the receptacle cavity 36 while the lead is chronically implanted within a patient's body. The side orientation of the diaphragm 40 away from the distal end of the lead assures that it is less likely to be in contact with the myocardium and in contact with blood in use.

Figure 11:
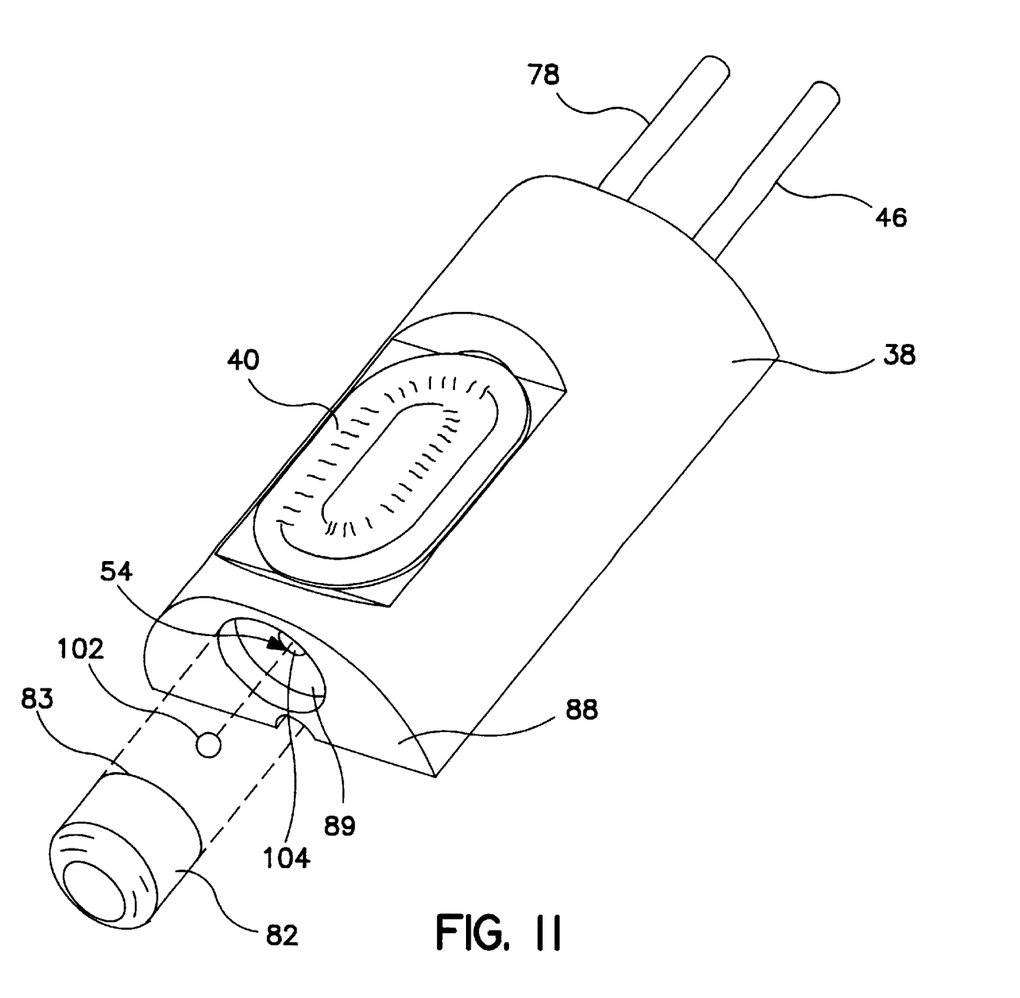
FIG. 11 is an exploded perspective view of a ball fitted into the fill tube lumen to seal the fill tube and a cover that is fitted over it and sealed to the end wall of the receptacle as shown in FIGS. 3–6.

FIG. 11 also depicts a modification to the diaphragm 40 incorporating corrugations or convolutions at least in part to assure a more linear deflection of the diaphragm 40 in the event that the oil within the receptacle cavity is pressurized somewhat by crimping or stopping of the fill tube. The corrugations allow the diaphragm 40 to be deflected more easily against the somewhat pressurized oil by pressure applied against its exterior surface.

The preceding specific embodiments are illustrative of the practice of the invention. It is to be understood, therefore, that other expedients known to those of skill in the art or disclosed herein may be employed without departing from the invention or the scope of the appended claims. It is therefore to be understood, that within the scope of the appended claims, the invention may be practiced otherwise than as specifically described without actually departing from the spirit and scope of the present invention.

What is claimed is:

1. A method of manufacturing an implantable pressure sensor mounted on a lead comprising the steps of:
   providing an elongated lead body having a lead body axis and a distal location for attachment with a pressure sensor module, said lead body having at least one lead conductor;
   forming a pressure sensor module comprising the further steps of:
      forming an elongated receptacle having an elongated receptacle cavity for receiving a calibrated, micro-machined pressure sensor transducer having a pressure responsive element, said receptacle formed of a base, oppositely disposed side walls and oppositely disposed end walls extending away from said base to form an opening frame adapted to be covered by a cover extending in parallel with said lead body axis;
      forming a fill port having a fill tube including a fill tube lumen extending outward from one of said end walls of said receptacle to a fill tube end;
      providing at least one electrical connector element extending into said receptacle cavity;
      disposing said pressure sensor within said receptacle cavity;
      electrically connecting said pressure sensor to said electrical connector element;
      sealing a diaphragm against said opening frame to enclose said receptacle cavity after said pressure sensor whereby said diaphragm is disposed along one side of the lead body at said distal location;
      filling said receptacle cavity via said fill port with an incompressible fluid for transmitting pressure applied outside said receptacle against said diaphragm to the pressure responsive element of said pressure sensor;
   closing said fill tube end to prevent leakage of said incompressible fluid from said receptacle cavity;
   fitting a fill port cover having an abutting edge over said crimped fill tube end and against one of said end walls to enclose said crimped fill tube end within a fill port cover cavity;
   sealing said abutting edge against said one of said end walls to hermetically enclose said crimped fill tube end within said fill port cover cavity; and
   attaching the pressure sensor module to the distal location of the lead body with said diaphragm disposed alongside said lead body and in parallel with said lead axis.

2. The method of claim 1 wherein said step of closing said fill tube end includes crimping said fill tube end to close said fill tube lumen and seal said fill tube to prevent leakage of said fluid from said receptacle cavity.

3. The method of claim 1 wherein said closing step further comprises the step of
   fitting a stopper into said fill tube end of said fill port lumen.

4. A method of manufacturing an implantable pressure sensor comprising the steps of:
   forming a receptacle having a receptacle cavity for receiving a calibrated, micro-machined pressure sensor transducer having a pressure responsive element, said receptacle having a base and side walls extending to an opening frame adapted to be covered by a cover and having a fill port extending through one side wall of said receptacle into said receptacle cavity coupled with a fill tube having a fill tube lumen extending outward of said side wall of said cavity to a fill tube end;
   disposing said pressure sensor transducer within said receptacle cavity;
   sealing a diaphragm against said opening frame to enclose said receptacle cavity, whereby said diaphragm is disposed along one side of a lead body at said distal location;
   filling said receptacle cavity with an incompressible fluid for transmitting pressure applied outside said receptacle against said diaphragm to the pressure responsive element of said pressure sensor;

crimping said fill tube end to close said fill tube lumen and seal said fill tube to inhibit leakage of said fluid from said receptacle cavity;

fitting a fill port cover having an abutting edge over the crimped fill tube end and against said side wall to enclose said crimped fill tube end within a fill port cover cavity; and sealing said abutting edge against said side wall to hermetically enclose said crimped fill tube end within said fill port cover cavity.

* * * * *